United States Patent
Krishnan et al.

(10) Patent No.: US 12,249,422 B2
(45) Date of Patent: Mar. 11, 2025

(54) METHOD AND SYSTEM FOR DETECTION AND VALIDATION OF NOCTURIA IN A PERSON

(71) Applicant: Tata Consultancy Services Limited, Mumbai (IN)

(72) Inventors: Balasubramaniam Krishnan, Bangalore (IN); Ramesh Balaji, Chennai (IN); Srinivasa Raghavan Venkatachari, Chennai (IN); Arun Vijayakumar, Kochi (IN); Harish Kumar Dhanasekaran, Chennai (IN)

(73) Assignee: Tata Consultancy Services Limited, Mumbai (IN)

( * ) Notice: Subject to any disclaimer, the term of this patent is extended or adjusted under 35 U.S.C. 154(b) by 422 days.

(21) Appl. No.: 17/755,124

(22) PCT Filed: Nov. 6, 2020

(86) PCT No.: PCT/IB2020/060449
§ 371 (c)(1),
(2) Date: Apr. 21, 2022

(87) PCT Pub. No.: WO2021/090251
PCT Pub. Date: May 14, 2021

(65) Prior Publication Data
US 2022/0384041 A1 Dec. 1, 2022

(30) Foreign Application Priority Data
Nov. 8, 2019 (IN) .............................. 201921045539

(51) Int. Cl.
*G16H 50/20* (2018.01)
*A61B 5/20* (2006.01)
*G16H 40/67* (2018.01)

(52) U.S. Cl.
CPC ............. *G16H 50/20* (2018.01); *A61B 5/202* (2013.01); *G16H 40/67* (2018.01)

(58) Field of Classification Search
CPC ......... G16H 50/20; G16H 40/37; A61B 5/202
(Continued)

(56) References Cited

U.S. PATENT DOCUMENTS 8,204,597 B2   6/2012  Gerber et al.
11,147,459 B2  10/2021 Sobol et al.
(Continued)

OTHER PUBLICATIONS

Hupper et al., "Quantification of Nighttime Micturition with an Ambulatory Sensor-Based System", IAnnu Int Conf IEE Eng Med Biol, Soc, Date: 2014, Pubmed, https://www.forum-urodynamicum.de/Eugen-Rehfisch-Preis/PDF/2015_abstract_09.pdf.
(Continued)

*Primary Examiner* — Nadia A Mahmood
(74) *Attorney, Agent, or Firm* — Finnegan, Henderson, Farabow, Garrett & Dunner, LLP (57) ABSTRACT

Nocturia has been defined as the need for an individual to wake up one or more times during the night to void. Further, Nocturia detection also requires analysis of sleeping pattern of the person. In such cases a lot of assumptions are made when the person is not in bedroom during nights. A method and system for detection and validation of Nocturia in the person has been provided. The system is utilizing a statistical based analysis, a rule based analysis, a machine learning based analysis and analysis of sleeping pattern of the person to detect and validate Nocturia. The system ensures that the person is not disturbed in his/her daily activities. Further, the processes deployed in the system are completely un-supervisory in nature meaning it does not have the dependency of needing to have trained machine learning dataset.

10 Claims, 4 Drawing Sheets

(58) Field of Classification Search
USPC .......................................................... 600/301
See application file for complete search history.

(56) References Cited

U.S. PATENT DOCUMENTS

| | | | | |
|---|---|---|---|---|
| 2008/0300449 | A1* | 12/2008 | Gerber | A61N 1/36007 |
| | | | | 600/30 |
| 2011/0105853 | A1 | 5/2011 | Raokowski et al. | |
| 2017/0095670 | A1* | 4/2017 | Ghaffari | A61M 21/02 |
| 2018/0286520 | A1* | 10/2018 | Apte | G16H 50/70 |
| 2019/0209022 | A1 | 6/2019 | Sobol et al. | |

OTHER PUBLICATIONS

Taramasco, Carla et al., "A Novel Low-Cost Sensor Prototype for Nocturia Monitoring in Older People", IEEE Access, Date: Sep. 2018, vol. 6, pp. 52500-52509, Publisher: IEEE, https://ieeexplore.ieee.org/stamp/stamp.jsp?tp=arnumber=8454452.

Boongird, Sarinya et al., "Nocturia and Aging: Diagnosis and Treatment", IEEE Access, Date: Jul. 2010, Publisher: Pubmed, https://www.ackdjournal.org/action/showPdf?pii=S1548-5595%2810%2900076-5.

Enshaeifar, Shirin et al., "Machine learning methods for detecting urinary tract infection and analysing daily living activities in people with dementia", IEEE Access, Date: Jan. 2019, vol. 14 (1), Publisher: PLoS One, https://www.researchgate.net/publication/330405021_Machine_learning_methods_for_detecting_urinary_tract_infection_and_analysing_daily_living_activties_in_people_with_dementia/link/5c3e8a0c92851c22a3785f44/download.

Eskofier, BM et al., "An ambulatory sensor-based system for quantification of nighttime micturition for accurate nocturia assessment", Conf. Proc. IEEE Eng Med Biol Soc. Aug. 2014 Publisher: Pubmed, https://www.informatik.uni-erlangen.de/Forschung/Publikationen/2014/Eskofier14-AAS.pdf.

International Search Report and Written Opinion mailed Mar. 25, 2021, in International Application No. PCT/IB2020/060449; 9 pages.

* cited by examiner

METHOD AND SYSTEM FOR DETECTION AND VALIDATION OF NOCTURIA IN A PERSON

CROSS-REFERENCE TO RELATED APPLICATIONS AND PRIORITY

This application is an US National Stage Filing and claims priority from International Application No. PCT/IB2020/060449, filed on Nov. 6, 2020, which application claims priority from Indian Provisional Patent Application No. 201921045539 filed on Nov. 8, 2019. The entire contents of the aforementioned applications are incorporated herein by reference.

TECHNICAL FIELD

The embodiments herein generally relate to the field of healthcare monitoring in individuals. More particularly, but not specifically, the present disclosure provides a method and system for detection and validation of nocturia in a person.

BACKGROUND

Nocturia has been defined as the need for an individual to wake up one or more times during the night to void (i.e. to urinate). The prevalence of nocturia varies markedly, depending on the age. Various studies have observed that the prevalence of nocturia increases with age, ranging from 4% in children aged 7 to 15 years to approximately 70% in adults aged >60 years.

The causes of nocturia are varied, involving both urologic and non-urologic conditions influenced by the aging process. There is an increasing role for nephrologists in managing nocturia in collaboration with urologists and primary care physicians because it may be the initial presenting symptom in chronic kidney disease (CKD), as well as other systemic diseases, such as congestive heart failure (CHF), diabetes mellitus (DM), or sleep disorders. Therefore, it is necessary to detect Nocturnal symptoms in the person as early as possible.

As per the recent definitions, Nocturia has also been shown to be associated with poor sleep quality and several types of sleep disorders, including obstructive and central apnea syndrome, and sleep disorders related to medical or neurologic diseases. Short and fragmented sleep has been associated with poor sleep quality, fatigue, daytime sleepiness, impaired daytime performance, and increased risk of cardiovascular disease events. Disturbed sleep in the elderly population and caregivers appeared to have a significant influence on the decision to institutionalize the elderly people.

In order to define treatment and measure therapeutic success in Nocturia, questionnaires are traditionally used for ambulatory assessment. However, questionnaires were reported to suffer from compliance, embarrassment and subjective bias.

Further, there are few other methods in the art which are used for Nocturia identification and detection, but those are not aligned with the latest clinical definition of Nocturia which takes sleep pattern into account. In the prior art, it has been seen that where lot of assumptions are made that when the person is not in bedroom during nights, he or she must have gone to bathroom and they approach bathroom visits through label data set and approach to predict the bathroom visits as the machine learning classification problem.

SUMMARY

Embodiments of the present disclosure present technological improvements as solutions to one or more of the above-mentioned technical problems recognized by the inventors in conventional systems.

In view of the foregoing, an embodiment herein provides a system for detection and validation of Nocturia in a person, the system comprises a plurality of sensors, one or more hardware processors and a memory in communication with the one or more hardware processors. The plurality of sensors present in one or more rooms and one or more bathrooms, wherein the plurality of sensors are configured to sense location of the person over a predefined number of days. The memory further configured to perform: receive a plurality of readings from the plurality of sensors; extract a plurality of features from the plurality of sensors readings; create a featured engineered sensor dataset using the plurality of features; apply a set of statistical techniques on the featured engineered sensor dataset to detect anomalies in the bathroom visit patterns wherein the anomalies are used to detect the presence of Nocturia in the person based on a first predefined criterion; apply a set of rules on the featured engineered sensor dataset to identify bathroom visit patterns, wherein the bathroom visit patterns are used to determine the presence of Nocturia in the person based on a second predefined criterion; apply a one support vector machine (SVM) classifier on the plurality of features to detect anomalies in the bathroom visit patterns, wherein the anomalies are used to detect the presence of Nocturia in the person; ensemble outputs obtained from the set of statistical techniques, the set of rules and the SVM classifier to identify whether the person is showing a positive Nocturia or a negative Nocturia depending on a third predefined criterion; identify anomalies in a sleeping pattern of the person using the featured engineered sensor dataset by applying a machine learning technique, wherein the sleeping pattern is either a positive or negative depending on a fourth predefined criterion; And, detect and validate the presence of Nocturia in the person if the person is showing positive Nocturia and the negative sleeping pattern.

In another aspect, the embodiment here provides a method for detection and validation of Nocturia in a person. Initially, readings are received from a plurality of sensors sensing location of the person over a predefined number of days, wherein the plurality of sensors are present in one or more rooms and one or more bathrooms. Further, a plurality of features is extracted from the plurality of sensors data. In the next step, a featured engineered sensor dataset is created using the plurality of features. Further, a set of statistical techniques are applied on the featured engineered sensor dataset to detect anomalies in the bathroom visit patterns wherein the anomalies are used to detect the presence of Nocturia in the person based on a first predefined criterion. Further, a set of rules are applied on the featured engineered sensor dataset to identify bathroom visit patterns, wherein the bathroom visit patterns are used to determine the presence of Nocturia in the person based on a second predefined criterion. In the next step, a one support vector machine (SVM) classifier is applied on the plurality of features to detect anomalies in the bathroom visit patterns, wherein the anomalies are used to detect the presence of Nocturia in the person. Further, outputs obtained from the set of statistical techniques, the set of rules and the SVM classifier are ensemble to identify whether the person is showing a positive Nocturia or a negative Nocturia depending on a third predefined criterion. In the next step, anomalies in a sleeping pattern of the person are identified using the featured engineered sensor dataset by applying a machine learning technique, wherein the sleeping pattern is either a positive or negative depending on a fourth predefined criterion. And finally, the presence of Nocturia is detected and validated in the person if the person is showing positive Nocturia and the negative sleeping pattern.

In yet another aspect, a non-transitory computer readable medium for detection and validation of Nocturia in a person. Initially, readings are received from a plurality of sensors sensing location of the person over a predefined number of days, wherein the plurality of sensors are present in one or more rooms and one or more bathrooms. Further, a plurality of features is extracted from the plurality of sensors data. In the next step, a featured engineered sensor dataset is created using the plurality of features. Further, a set of statistical techniques are applied on the featured engineered sensor dataset to detect anomalies in the bathroom visit patterns wherein the anomalies are used to detect the presence of Nocturia in the person based on a first predefined criterion. Further, a set of rules are applied on the featured engineered sensor dataset to identify bathroom visit patterns, wherein the bathroom visit patterns are used to determine the presence of Nocturia in the person based on a second predefined criterion. In the next step, a one support vector machine (SVM) classifier is applied on the plurality of features to detect anomalies in the bathroom visit patterns, wherein the anomalies are used to detect the presence of Nocturia in the person. Further, outputs obtained from the set of statistical techniques, the set of rules and the SVM classifier are ensemble to identify whether the person is showing a positive Nocturia or a negative Nocturia depending on a third predefined criterion. In the next step, anomalies in a sleeping pattern of the person are identified using the featured engineered sensor dataset by applying a machine learning technique, wherein the sleeping pattern is either a positive or negative depending on a fourth predefined criterion. And finally, the presence of Nocturia is detected and validated in the person if the person is showing positive Nocturia and the negative sleeping pattern.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Figure 1:
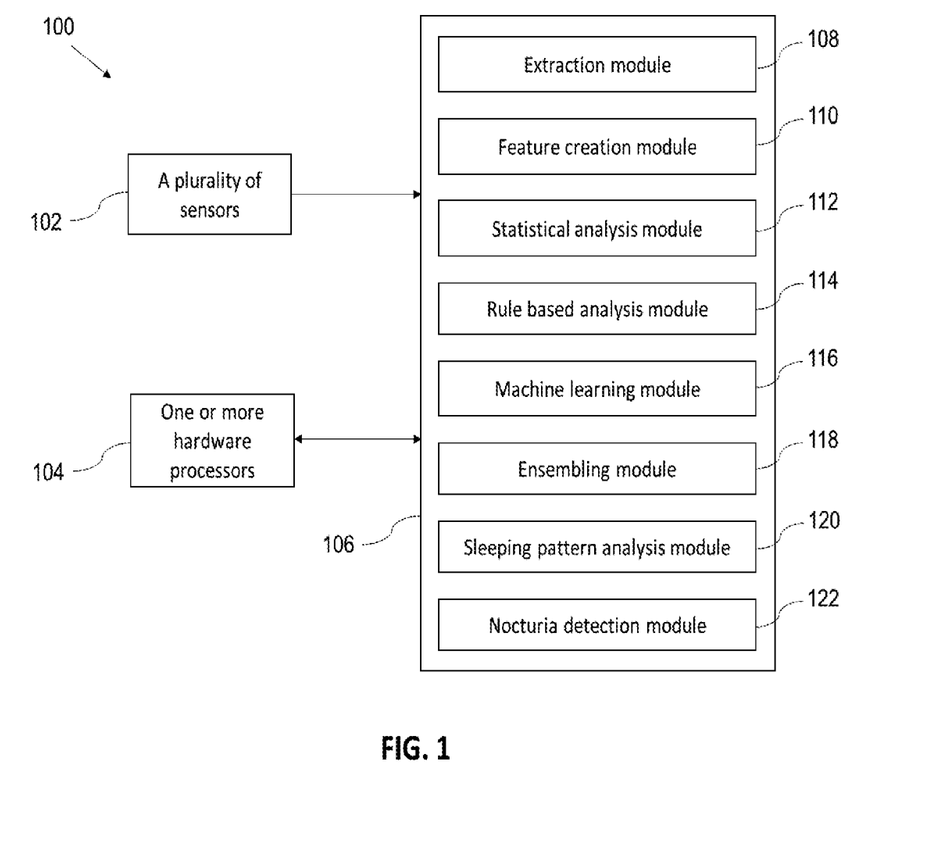
FIG. 1 shows a block diagram of a system for detection and validation of nocturia in a person according to an embodiment of the present disclosure.
Figure 2:
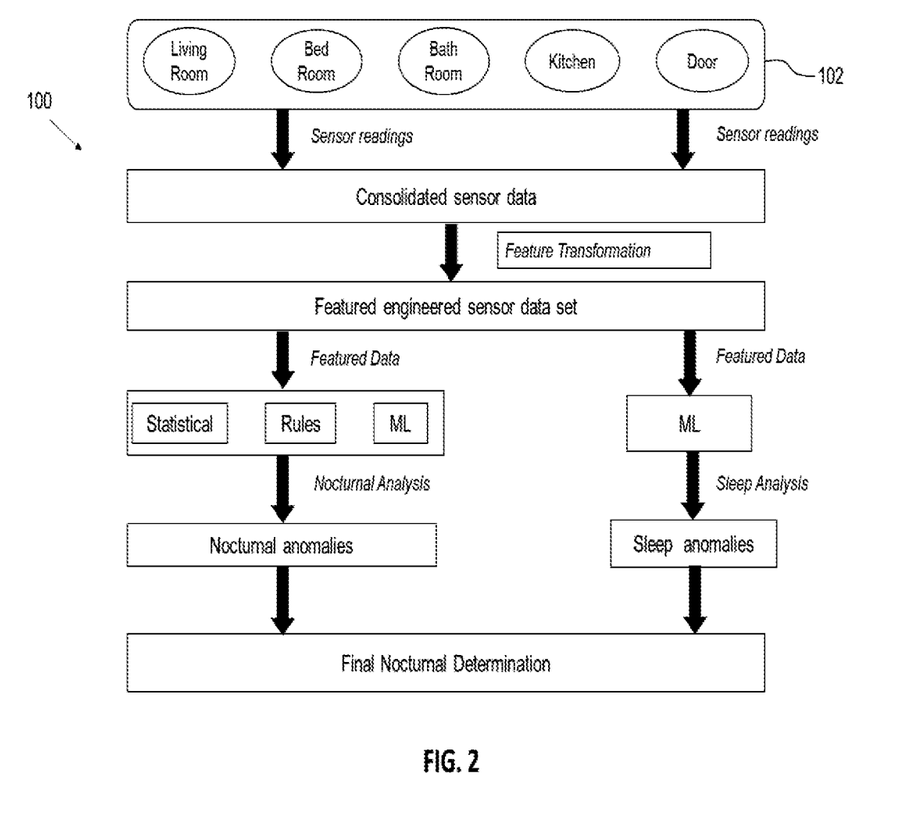
FIG. 2 shows an architectural view of the system for detection and validation of Nocturia in the person according to an embodiment of the disclosure.
Figure 3A:
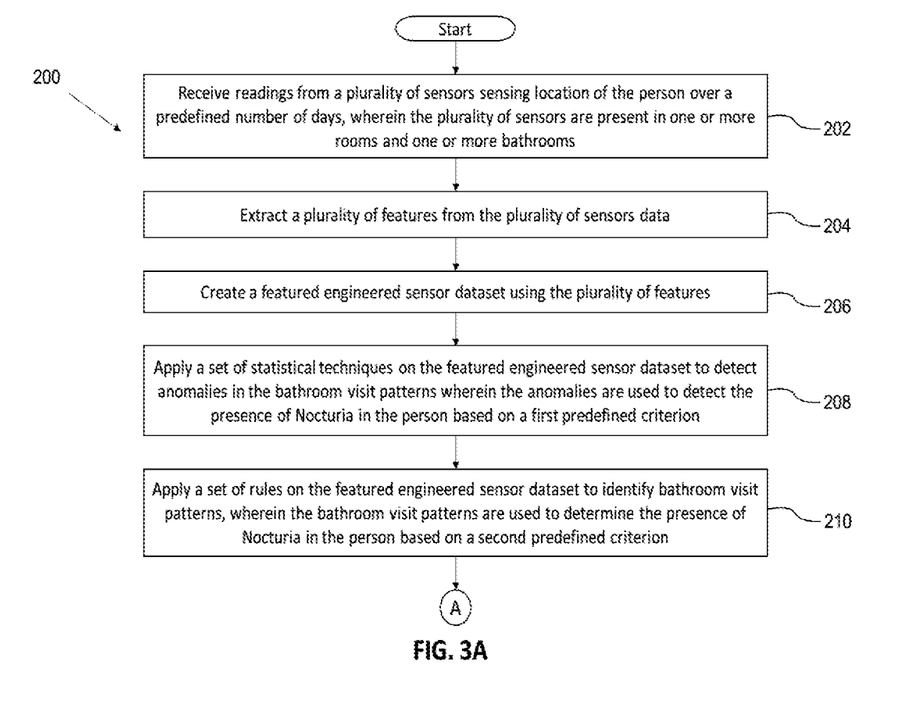
FIG. 3A-3B shows a flowchart illustrating the steps involved in detection and validation of nocturia in a person according to an embodiment of the present disclosure.
Figure 3B:
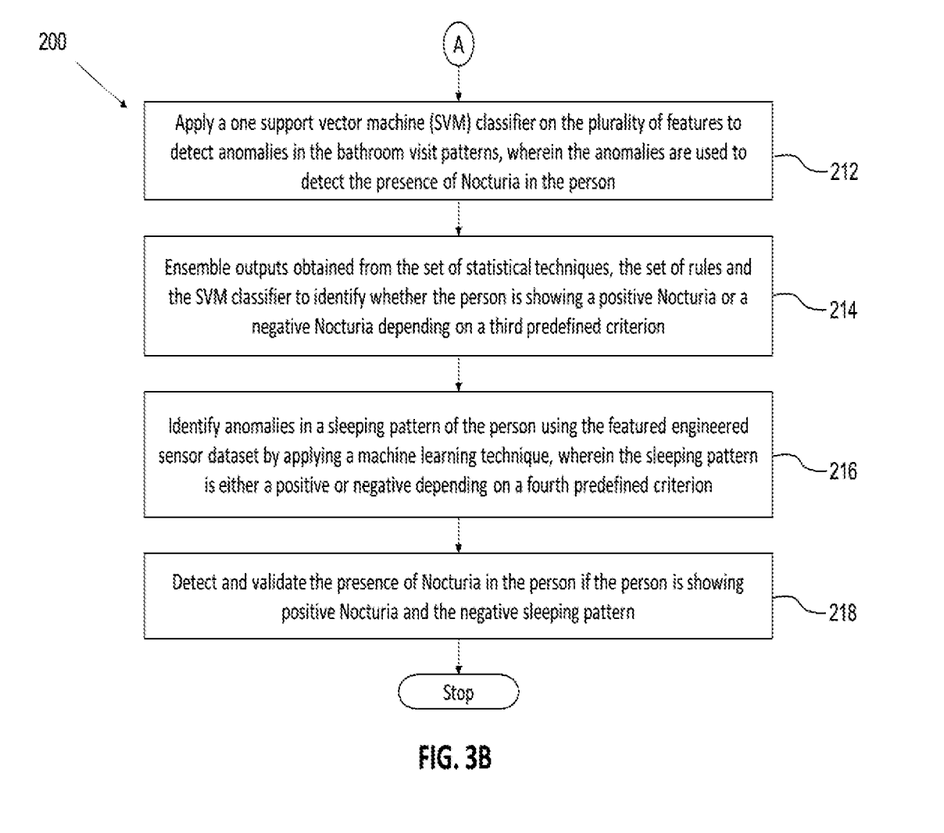

Referring now to the drawings, and more particularly to FIG. 1 through FIG. 3, where similar reference characters denote corresponding features consistently throughout the figures, there are shown preferred embodiments and these embodiments are described in the context of the following exemplary system and/or method.

According to an embodiment of the disclosure, a system 100 for detection and validation of nocturia in a person is shown in the block diagram of FIG. 1. An architectural overview of the system 100 is shown in the FIG. 2. The system 100 is utilizing an approach to detect and validate the Nocturnal symptoms using three processes, i.e., a statistical based analysis, a rule based analysis and a machine learning based analysis. In addition to that, the system 100 is also configured to analyze the sleep pattern of the person as shown in FIG. 2. Based on the output of three processes and sleeping pattern analysis an accurate Nocturia detection and validation can be performed so that right intervention can be applied to the person. The system 100 ensures that the person is not disturbed in his/her daily activities. Further, the processes deployed in the system 100 are completely unsupervisory in nature meaning it does not have the dependency of needing to have trained machine learning dataset.

It should be appreciated that the system 100 of the present disclosure has been implemented in a facility such as an old age home, a hospital or a home etc. In an example the facility might be a home where a person above the age of 65 is living alone and independently. This home has the plurality of sensors fixed in all the locations that include living room, bedroom, kitchen & bathroom as shown in FIG. 2. Though the system 100 can also be used in any other facility by a person skilled in the art.

According to an embodiment of the disclosure, the system 100 comprises a plurality of sensors 102, one or more hardware processors 104 and a memory 106 in communication with the one or more hardware processors 104 as shown in the block diagram of FIG. 1. The one or more hardware processors 104 work in communication with the memory 106. The one or more hardware processors 104 are configured to execute a plurality of algorithms stored in the memory 106. The memory 106 further includes a plurality of modules for performing various functions. The memory 106 comprises an extraction module 108, a feature creation module 110, a statistical analysis module 112, a rule based analysis module 114, a machine learning module 116, an ensembling module 118, a sleeping pattern analysis module 120 and a Nocturia detection module 122. The memory 108 may further comprise other modules for performing certain functions.

The plurality of sensors 102 are located at various places in the one or more rooms and one or more bathrooms. The plurality of sensors 102 are located in multiple rooms and their entry and exit points. The plurality of sensors 102 is configured to detect the location and movement of the person inside the rooms and bathroom. The plurality of sensors 102 is configured to provide readings of the movement of the person over a predefined number of days. These readings are referred as the consolidated senor data. In an example, 90 days have been utilized to get the readings.

According to an embodiment of the disclosure, the memory 106 comprises the extraction module 108 and the feature creation module 110. The extraction module 108 is configured to extract a plurality of features from the plurality of sensors 102. The feature creation module 110 is configured to create a featured engineered sensor dataset using the extracted plurality of features, which may also be referred as a featured engineered sensor output. The extraction module 108 and the feature creation module 110 basically takes the raw sensor data as input and create as many features as possible so that it makes the dataset very detailed and clear. The clarity in coming up with featured engineered dataset will itself reveal the nightly bathroom patterns in more simplistic way.

According to an embodiment of the disclosure, each of the plurality of sensors 102 has a unique sensor ID. Accordingly, each of the sensor data collected from the plurality of sensor has a sensor ID, sensor date and sensor time corresponding to date and time respectively on which sensor data is collected, and sensor location where the sensor is located in the one or more rooms and one or more bathrooms.

The featured engineered sensor dataset includes but not limited to sensor ID, sensor date, hour, minute, second, day, week, month, year, weekday/weekend. In addition to that the featured engineered sensor dataset will also tell about the location of the person from where he/she has started (FromLocation) and went to which location (Tolocation). The featured engineered sensor dataset also tells the time spent by the person in the room (Timespent), if there is change in room by the person (RoomChangeIndicator), and day time or night time (Y/N)" etc. Every row in raw sensor data is converted into the above data structure. If the raw sensor data has 1000 rows for 3 months as an example, this will have 3 months of enriched features. The featured engineered sensor dataset by looking at it generally can clearly tell where the person spent his time.

For example, FromLocation and Tolocation got data values like "Bedroom", which means the person is spending his time in bedroom and during that time, the room change indicator which is another feature will have "N" value. However, if the person moves from living room to bathroom, the FromLocation will have "Living Room" and ToLocation will have "Bathroom" and "RoomChangeIndicator" will have "Y" value.

The featured engineered sensor dataset captures data if the person is moving from which ever room during night time to bathroom. There is no need to make any assumption and the resident is not in bedroom means he is in bathroom and with this enriched structure. The same can be represented as follows:

Sum of Raw Sensor Data for "n" number of days (d1, d2, d3, . . . dn)

X_SRn=xsrd1+xsrd2+xsrd3+ . . . xsrdn

Where, X_SRn is input to Feature Engineering function (FE_func) which gives a featured engineered sensor dataset (Z_FESD)

Z_FESD=FE_func(X_SRn)

According to an embodiment of the disclosure, the memory 106 comprises the statistical analysis module 112. The statistical analysis module 112 performs the first process for detecting Nocturnal symptoms. The statistical analysis module 112 is configured to apply a set of statistical techniques on the featured engineered sensor dataset to detect anomalies in the bathroom visit patterns wherein the anomalies are used to detect the presence of nocturia in the person based on a first predefined criterion. The first predefined criterion is the coefficient of variance of the number of times person visiting the bathroom is more than one.

The system 100 can deduce the bathroom visit patterns of the person from the featured engineered sensor dataset by querying as follows:

Tolocation="Bathroom", RoomChangeInd="Y" & Daytime="N"

This query gives a result set with all sensor data with above conditions sorted by week number for the predefined time period. This captures only the visits of the person visiting the bathroom not how much time he/she spent in the bathroom. Let the result set of above query as ResultCofVariance. Further the coefficient of variance is applied on the above result set which means CoeficientofVariance_Nocturia=Sd(ResultCofVariance)/mean(ResultCofVariance)

If CoeficientofVariance_Nocturia>1:
  NocturiaSymptom="Y"
Else
  NocturiaSymptom="N"

If the standard deviation of person's bathroom visits goes beyond the average bathroom visits, then it can potentially be a Nocturia symptom.

This can be expressed in algorithmic representation as follows: The featured engineered sensor dataset is passed as input to function NF_Stat. NF_Stat refers to finding nocturnal patterns from statistical technique. NF_Stat will return a binary output 1 or 0. Z_NP1 refers to output of Nocturnal Process 1

1 refers to +ve Nocturnal Pattern
0 refers to −ve Nocturnal Pattern
Z_NP1 (1,0)=NF_Stat(ZFESD)

According to an embodiment of the disclosure, the memory 106 comprises the rule based analysis module 114. The rule based analysis module 114 performs the second process for detecting Nocturnal symptoms. The rule based analysis module 114 is configured to apply a set of rules on the featured engineered sensor dataset to identify bathroom visit patterns, wherein the bathroom visit patterns are used to determine the presence of nocturia in the person based on a second predefined criterion. In an example, the second predefined criterion is the person visited bathroom more than 3 times in a night on last 2 weeks for more than 3 days.

To capture that the person's recent behavior in terms of his/her bathroom visits, following query is applied on the featured engineered sensor dataset:

Tolocation="Bathroom", RoomChangeInd="Y" & Daytime="N"

Let's call this as "FirstResult". Further, the "FirstResult" is split as "Week", "Days of Week", and "Bathroom Visits". This result set provides information on every week, on each day of every week, how many bathroom visits happened. This dataset is called as "SecondResult".

Further, another query is applied on "SecondResult" dataset as shown in the following example: No. of bathroom visits greater than 3 (configurable) and where week includes last 2 week numbers and day count is more than 3, i.e. if the person visited bathroom more than 3 times in a night on last 2 weeks for more than 3 days in that week he can potentially having a Nocturnal pattern. The algorithmic representation of same is as follows:

The featured engineered sensor dataset is passed as an input to function NF_Rule. NF_Rule refers to finding nocturnal patterns from rule based technique. NF_Rule will return a binary output 1 or 0. Z_NP2 refers to output of Nocturnal Process.

Z_NP2(1,0)=NF_Rule(ZFESD)

1 refers to +ve Nocturnal Pattern 0 refers to −ve Nocturnal Pattern

According to an embodiment of the disclosure, the memory 106 comprises the machine learning module 116. The machine learning module 116 performs the first process for detecting Nocturnal symptoms. The machine learning module 116 is configured to apply a one support vector machine (SVM) classifier on the plurality of features to detect anomalies in the bathroom visit patterns, wherein the anomalies are used to detect the presence of Nocturia in the person. This was done to understand the anomalies in bathroom visit patterns. Another query is applied on the featured engineered sensor dataset as follows:

Tolocation="Bathroom", RoomChangeInd="Y" & Daytime="N",

Let's call this as "ThirdResult". The "ThirdResult" is split further as "Week", "Bathroom Visits". This result tells on every week, how many bathroom visits happened, this dataset is called as "FourthResult". On the FourthResult, the one SVM classifier is applied. The one SVM classifier detects anomalies purely based on the fact that anomalies are data points and data densities. When applying the one SVM classifier model, contamination is set as outliers_fraction, that is telling the model that the proportion of outliers in the data set which is going to be put as "0.01". The anomalies will be output of the one SVM classifier model. This data points will be analyzed with high number of bathroom visits. The algorithmic representation of same is as follows: Featured engineered sensor dataset is passed as input to function NF_ML. NF_ML refers to finding Nocturnal patterns from machine learning (ML) based technique. The ML technique will be one SVM classifier as it is able to identify patterns in unsupervised manner with anomalies not only based on data but also on data densities. It also works well on Non Linear situations. NF_ML returns a binary output 1 or 0. Z_NP3 refers to output of machine learning module 116.

Z_NP3(1,0)=NF_ML(ZFESD)

1 refers to +ve Nocturnal Pattern 0 refers to −ve Nocturnal Pattern

According to an embodiment of the disclosure, the memory 106 further comprises the ensembling module 118. The ensembling module 118 is configured to ensemble outputs obtained from the processes performed using the set of statistical techniques, the set of rules and the SVM classifier to identify whether the person is showing a positive Nocturia or a negative Nocturia depending on a third predefined criterion. The third predefined criterion comprising: identifying the Nocturia as positive if at least two of the set of statistical techniques, the set of rules and the one SVM classifier are showing the presence of Nocturia.

The ensembling module 118 looks at the results of the statistical analysis module 112, the rule based analysis module 114 and the machine learning module 116 and find out, that in out of three processes, how many came up with Nocturnal pattern with value 1. As each process will return a value of 1 +ve Nocturnal pattern or 0 which is −ve Nocturnal pattern. To ensure a personal is Nocturnal from the above processes, at least two processes returning the value of 1 then only it can be determined that the person has indication of Nocturia. Otherwise, if at least two processes return a value of 0 then it can be ruled out Nocturnal pattern from the person. The ensemble process is efficient that it does bring down "false positives". The algorithmic representation of same is as follows:

Z_NPE=(if Sum (Z_NP1,Z_NP2,Z_NP3)>=2) then 1 else 0;

1 refers to +ve Nocturnal Pattern 0 refers to −ve Nocturnal Pattern where, Z_NPE refers to output of final nocturnal ensemble coming out of the ensemble. Z_NPE will give the binary output of either 1, if the sum of binary output of the first process, the second process and the third process returns a value 2 or more than 2 which means a +ve Nocturnal indicator. Now if the sum of binary output of the first process, the second process and the third process returns a value less than 2 which means a −ve Nocturnal indicator.

According to an embodiment of the disclosure, the memory 106 comprises the sleeping pattern analysis module 120. The sleeping pattern analysis module 120 is configured to identify anomalies in a sleeping pattern of the person using the featured engineered sensor dataset by applying a machine learning technique, wherein the sleeping pattern is either a positive or negative depending on a fourth predefined criterion. The fourth predefined criterion is a specific number of hours spent continuously in a bedroom during the night. The specific number of hours are pre-decided and are set between six to nine hours.

The sleep pattern anomalies are determined through ML based technique. The ML technique will be one SVM classifier as it is able to identify patterns in unsupervised manner with anomalies not only based on data but also on data densities. It also works well on non-linear situations. Before applying the ML technique, it needs to be made sure that the person stayed in bedroom for sleep. This can be answered from featured engineered sensor dataset by querying as follows:

FromLocation="Bed", ToLocation="Bed", RoomChangeInd="N" & Daytime="N"

The above query gives a dataset with all sensor data of person's sleep time, let's call this as FifthResult. The "FifthResult" is split further as "Week", "Time Spent in Bed". This result set tells on every week, how hours he spent on the bedroom. This is called as SixthResult. The ML technique one SVM classifier is deployed on SixthResult. The one SVM classifier detects anomalies based on the fact that anomalies are data points and data densities. When applying the one SVM classifier model, contamination is set as outliers_fraction, that is telling the model that the proportion of outliers in the data set is "0.01". The anomalies will be the output of the one SVM classifier model. This data points will be analyzed for Sleep anomalies. Following is the Algorithmic representation:

Featured Engineered Dataset is passed as input to function SF_ML. SF_ML refers to finding sleep patterns from Machine learning based Technique. SF_ML will return a binary output 1 or 0 (SF refers to sleep function). Z_SP refers to output of Sleep Pattern.

Z_SP=SF_ML (ZFESD)

1 refers to +ve sleep Pattern 0 refers to −ve sleep Pattern

According to an embodiment of the disclosure, the memory 106 further comprises the Nocturia detection module 122. The Nocturia detection module 122 is configured to detect and validate the presence of nocturia in the person if the person is showing positive Nocturia and the negative sleeping pattern.

The anomalies of sleep function determined by output Z_PF and nocturnal anomalies through Z_NP3 are correlated. For the correlation, Pearson correlation function is deployed. This inverse correlation is observed i.e. pattern with high bathroom visits translates to disturbance in sleep. Following is the Algorithmic representation:

CorSN=CorrFunc(Z_SP,Z_NP3)

As part of final check, once CorSN comes as Inverse Correlation and final ensemble is determined as 1 i.e. nocturnal indicator, the person is detected as Nocturnal indicator else the person is determined as No Nocturnal indicator.

If CorSN==−1 & Z_NPE=1
FinalNocturia=Yes
Else,
FinalNocturia=No

In operation, a flowchart 200 illustrating a method for detection and validation of Nocturia in a person is shown in FIG. 3A-3B. Initially at step 202, readings are received from a plurality of sensors sensing location of the person over a predefined number of days. The plurality of sensors are present in one or more rooms and one or more bathrooms. The one or more rooms and one or more bathrooms is normally present in a facility such as old age home, hospitals etc. At step 204, a plurality of features is extracted from the plurality of sensors data. At step 206, the featured engineered sensor dataset is created using the plurality of features. The featured engineered sensor dataset may include but not limited to sensor ID, sensor date, hour, minute, second, day, week, month, year, weekday/weekend.

At step 208, a set of statistical techniques on the featured engineered sensor dataset is applied to detect anomalies in the bathroom visit patterns wherein the anomalies are used to detect the presence of Nocturia in the person based on a first predefined criterion. This is the first process used to detect the Nocturnal symptoms.

At step 210, a set of rules on the featured engineered sensor dataset is applied to identify bathroom visit patterns, wherein the bathroom visit patterns are used to determine the presence of Nocturia in the person based on a second predefined criterion. This is the $2^{nd}$ process used to detect the Nocturnal symptoms.

At step 212, a one support vector machine (SVM) classifier is applied on the plurality of features to detect anomalies in the bathroom visit patterns, wherein the anomalies are used to detect the presence of Nocturia in the person. This is the third process used to detect the Nocturnal symptoms.

A step 214, the outputs obtained from the set of statistical techniques, the set of rules and the SVM classifier are ensemble to identify whether the person is showing a positive Nocturia or a negative Nocturia depending on a third predefined criterion. At step 216, anomalies in a sleeping pattern of the person are identified using the featured engineered sensor dataset by applying a machine learning technique, wherein the sleeping pattern is either a positive or negative depending on a fourth predefined criterion. And finally at step 218, the presence of Nocturia in the person is detected and validated if the person is showing positive Nocturia and the negative sleeping pattern.

Thus, the present disclosure utilizing the techniques are which completely "unsupervisory" in nature meaning it does not have the dependency of needing to have trained ML dataset. Further, Conclusions is not based on the output of just one technique. The Nocturnal results are selected based on the maximum votes which is efficient technique that is normally applied by ML Algorithms like Random Forest.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of the present disclosure herein solve the problems of inaccurate Nocturia detection due to the use of only one technique. The disclosure provides a method and system for detection and validation of nocturia in a person.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

We claim:

1. A processor implemented method for detection and validation of Nocturia in a person, the method comprising:
   receiving readings from a plurality of sensors sensing location of the person over a predefined number of days, wherein the plurality of sensors are present in one or more rooms and one or more bathrooms;
   extracting, via one or more hardware processors, a plurality of features from the plurality of sensors data;
   creating, via one or more hardware processors, a featured engineered sensor dataset using the plurality of features;
   applying, via one or more hardware processors, a set of statistical techniques on the featured engineered sensor dataset to detect anomalies in the bathroom visit patterns wherein the anomalies are used to detect the presence of Nocturia in the person based on a first predefined criterion;
   applying, via one or more hardware processors, a set of rules on the featured engineered sensor dataset to identify bathroom visit patterns, wherein the bathroom visit patterns are used to determine the presence of Nocturia in the person based on a second predefined criterion;
   applying, via one or more hardware processors, a one support vector machine (SVM) classifier on the plurality of features to detect anomalies in the bathroom visit patterns, wherein the anomalies are used to detect the presence of Nocturia in the person;
   ensembling, via one or more hardware processors, outputs obtained from the set of statistical techniques, the set of rules and the SVM classifier to identify whether the person is showing a positive Nocturia or a negative Nocturia depending on a third predefined criterion;
   identifying, via one or more hardware processors, anomalies in a sleeping pattern of the person using the featured engineered sensor dataset by applying a machine learning technique, wherein the sleeping pattern is either a positive or negative depending on a fourth predefined criterion, wherein the anomalies in the bathroom visit patterns are identified based on data points and data densities in the featured engineered sensor dataset; and
   detecting and validating, via one or more hardware processors, the presence of Nocturia in the person if the person is showing positive Nocturia and the negative sleeping pattern.

2. The method of claim 1 further comprising detecting and validating the presence of Nocturia in the person using a Pearson correlation function.

3. The method of claim 1, wherein each reading of the plurality of sensor readings comprises a sensor id from which reading is captured, location of the sensor and the date of the sensor reading.

4. The method of claim 1, where in the anomalies in the number of visits in the one or more bathrooms is represented by coefficient of variance.

5. The method of claim 1, wherein the second predefined criterion is the person visited bathroom more than 3 times in a night on last 2 weeks for more than 3 days.

6. The method of claim 1, wherein the third predefined criterion comprising: identifying the Nocturia as positive if at least two of the set of statistical techniques, the set of rules and the one SVM classifier are showing the presence of Nocturia.

7. The method of claim 1, wherein the fourth predefined criterion is a specific number of hours spent continuously in a bedroom during the night.

8. The method of claim 1, wherein the plurality of features includes "SensorID", date, hour, minute, second, day, week, month, year, weekday/weekend, start location, end location, time spent, room change indicator, daytime indicator.

9. A system for detection and validation of Nocturia in a person, the system comprises:
   a plurality of sensors present in one or more rooms and one or more bathrooms, wherein the plurality of sensors are configured to sense location of the person over a predefined number of days;
   one or more hardware processors; and
   a memory in communication with the one or more hardware processors, the memory configured to perform:
      receive a plurality of readings from the plurality of sensors;
      extract a plurality of features from the plurality of readings;
      create a featured engineered sensor dataset using the plurality of features;
      apply a set of statistical techniques on the featured engineered sensor dataset to detect anomalies in the bathroom visit patterns wherein the anomalies are used to detect the presence of Nocturia in the person based on a first predefined criterion;
      apply a set of rules on the featured engineered sensor dataset to identify bathroom visit patterns, wherein the bathroom visit patterns are used to determine the presence of Nocturia in the person based on a second predefined criterion;
      apply a one support vector machine (SVM) classifier on the plurality of features to detect anomalies in the bathroom visit patterns, wherein the anomalies are used to detect the presence of Nocturia in the person;
      ensemble outputs obtained from the set of statistical techniques, the set of rules and the SVM classifier to identify whether the person is showing a positive Nocturia or a negative Nocturia depending on a third predefined criterion;
      identify anomalies in a sleeping pattern of the person using the featured engineered sensor dataset by applying a machine learning technique, wherein the sleeping pattern is either a positive or negative depending on a fourth predefined criterion, wherein the anomalies in the bathroom visit patterns are identified based on data points and data densities in the featured engineered sensor dataset; and
      detect and validate the presence of Nocturia in the person if the person is showing positive Nocturia and the negative sleeping pattern.

10. A computer program product comprising a non-transitory computer readable medium having a computer readable program embodied therein, wherein the computer readable program, when executed on a computing device, causes the computing device to:

receiving readings from a plurality of sensors sensing location of the person over a predefined number of days, wherein the plurality of sensors are present in one or more rooms and one or more bathrooms;

extracting a plurality of features from the plurality of sensors data;

creating a featured engineered sensor dataset using the plurality of features;

applying a set of statistical techniques on the featured engineered sensor dataset to detect anomalies in the bathroom visit patterns wherein the anomalies are used to detect the presence of Nocturia in the person based on a first predefined criterion;

applying a set of rules on the featured engineered sensor dataset to identify bathroom visit patterns, wherein the bathroom visit patterns are used to determine the presence of Nocturia in the person based on a second predefined criterion;

applying a one support vector machine (SVM) classifier on the plurality of features to detect anomalies in the bathroom visit patterns, wherein the anomalies are used to detect the presence of Nocturia in the person;

ensembling outputs obtained from the set of statistical techniques, the set of rules and the SVM classifier to identify whether the person is showing a positive Nocturia or a negative Nocturia depending on a third predefined criterion;

identifying anomalies in a sleeping pattern of the person using the featured engineered sensor dataset by applying a machine learning technique, wherein the sleeping pattern is either a positive or negative depending on a fourth predefined criterion, wherein the anomalies in the bathroom visit patterns are identified based on data points and data densities in the featured engineered sensor dataset; and     detecting and validating, the presence of Nocturia in the person if the person is showing positive Nocturia and the negative sleeping pattern.

\* \* \* \* \*